United States Patent [19]

Weaver

[11] 4,399,219
[45] * Aug. 16, 1983

[54] PROCESS FOR ISOLATING MICROBIOLOGICALLY ACTIVE MATERIAL

[75] Inventor: James C. Weaver, Sudbury, Mass.

[73] Assignee: Massachusetts Institute of Technology, Cambridge, Mass.

[*] Notice: The portion of the term of this patent subsequent to Aug. 30, 2000, has been disclaimed.

[21] Appl. No.: 229,484

[22] Filed: Jan. 29, 1981

[51] Int. Cl.$^3$ .................... C12Q 1/04; C12Q 1/18; C12Q 1/06; C12M 1/34
[52] U.S. Cl. .................................. 435/34; 435/29; 435/32; 435/39; 435/291; 435/808
[58] Field of Search ............... 435/34, 39, 291, 808, 435/32, 29

[56] References Cited

U.S. PATENT DOCUMENTS

| | | | |
|---|---|---|---|
| 3,560,754 | 2/1971 | Kamentsky | 55/101 X |
| 3,710,933 | 1/1973 | Fulwyler et al. | 424/3 X |
| 3,790,492 | 2/1974 | Fulwyler | 264/0.5 X |
| 4,162,282 | 7/1979 | Fulwyler et al. | 264/101 X |
| 4,242,447 | 12/1980 | Findl et al. | 435/291 X |

Primary Examiner—Robert J. Warden
Attorney, Agent, or Firm—Arthur A. Smith, Jr.; Thomas J. Engellenner; Paul J. Cook

[57] ABSTRACT

Molecules or cells of materials exhibiting a microbiological activity, suppression or interaction of interest are isolated from a large population of similar molecules, cells or the like. The activity of the microbiologically active molecules or living matter of interest is measured by suspending the population in a liquid medium capable of forming a gel. The resultant suspension is formed into droplets which are caused to gel. The gel droplets (GMDs) are treated to effect desirable alteration of the microbiologically active material and the amount of metabolites or reaction products of the desired alteration within each of the gel droplets. Alternatively, incubation is carried out such that each GMD initially containing one cell contains many, a microcolony, which can be tested for desirable properties while retaining sufficient viable cells for further growth and harvesting for further tesing and/or production. The gel droplets are then separated based upon the measured or sensed characteristic, metabolite or reaction product.

25 Claims, No Drawings

PROCESS FOR ISOLATING MICROBIOLOGICALLY ACTIVE MATERIAL

BACKGROUND OF THE INVENTION

This invention relates to a process for isolating microbiologically active material such as bacteria.

Presently, there are available a wide variety of apparatus for isolating relatively large microbiologically active materials such as cells on the basis of a measured physical characteristic of the cell which in turn has relavance to the biological nature of the cell. Generally, these apparatus operate by first forming a stream of cells suspended in a liquid wherein the cells are sufficiently diluted and the stream is sufficiently small such that the cells pass by a point along the flow stream path one by one. Means are provided along the flow path to sense a physical characteristic of the cell which provides a measure of a particular desired biological characteristic of the cell. Examples of such physical measurements include light scattering, electrical impedance, fluorescence intensity, light absorption or fluorescence polarization. The stream of cells passes by the means for measuring the cell physical characteristic which measurement means is adapted to control flow of the cell stream so that the individual cells characterized by a physical measurement within a desired range can be separated and isolated from the stream. In one class of class of such apparatus, a portion of the cell stream is diverted into a secondary stream such as with a syringe. In another class of such apparatus, the cell stream is divided into droplets each of which has a high probability for containing none or a single cell. The droplets are formed by any conventional means such as a piezoelectric crystal and the droplets containing the desired cells are charged electrically while the remaining droplets are uncharged so that the charged droplets can be isolated from the remaining droplets such as with a set of conventional deflection plates. The charged droplets so recovered contain the desired cells at a far higher concentration that in the original stream.

Rotman, *Proceedings National Academy of Sciences*, Vol. 47, pgs. 1981–1991, 1961 discloses the formation of water droplets in oil which droplets contain a small number, often one, of enzymes. However, this procedure is very tedious, difficult to replicate and the enzymes are susceptible to migration from the droplets to the oil-water interface.

While the present procedures have been highly satisfactory for concentrating animal cells of desired characteristics, these procedures have not been as satisfactory for isolating biological material of a smaller size than animal cells, such as bacteria or enzymes. This is because the physical characteristics of these smaller colume particles or molecules are much more difficult to measure accurately, particularly at the flow rates available with present cell sorters. Accordingly, it would be highly desirable to provide a means for concentrating and isolating materials having microbiological activity which materials have a size much smaller than the normal size of eucaryote cells even on a molecular size basis. Furthermore, it would be desirable to provide such a process wherein a microbiologically active molecule cell or the like having an activity of interest can be isolated alone from a large population of similar microbiologically active materials.

SUMMARY OF THE INVENTION

In accordance with this invention, microbiologically active materials are suspended at a dilute concentration in a medium which can be subsequently converted to a gel micro droplet medium being a size between about $0.2\mu$ to $1000\mu$, preferably between about $5\mu$ and $100\mu$. The suspending medium is capable of substantially preventing degradation of the microbiologically active molecules, cells or the like, or of supporting growth of the microbiologically active matter such as in the case of bacteria. The dilute suspension then is formed into small droplets such as be being forced through a nozzle to form a liquid stream which then is sheared to form small liquid droplets, each of which has a high probability of containing a desired small number of molecules of cells or less. Thus, for example, each droplet can contain zero or one microbiologically active molecule or cell of interest with or without microbiologically active molecules or cells which coact with the molecule or cell of interest by regulating the degree of dilution of the liquid composition is processed and the average size of the GMD produced. The droplets formed then are changed in temperature or directed into a second liquid or vapor medium wherein the droplets rapidly gel. The change in temperature or second liquid or vapor medium is capable of converting the droplets to gel form either by temperature change or by contact with a vapor, while preventing degradation of the microbiologically active material. In the case that the liquid droplets are caused to gel before encountering liquid medium, gel micro-droplets (GMDs) can be directed onto a solid surface. The GMDs are treated in a manner to effect a desirable alteration of the microbiologically active material such as by incubation or by exposure to conventional marker molecules such as to a fluorescent stain or by exposure to a mutagenic environment or the like. The suspension of gel micro-droplets suitably diluted then is processed through an apparatus which forms a stream of the micro-droplets such that the micro-droplets pass an analyzer one by one so that each micro-droplet can be analyzed for a desired chemical or physical characteristic. Furthermore, the apparatus is capable of separating gel micro-droplets having the desired characteristics from the remainder of the stream in response to a signal from the onstream analyzer. Alternatively, measurements can be made on GMDs on a surface by scanning with a suitable light source or other means, in order to measure and distinguish desirable physical characteristics. Subsequent to such scanning, the GMDs with desired physical characteristics can be mechanically removed and thereby isolated.

DESCRIPTION OF SPECIFIC EMBODIMENTS

In accordance with this invention, microbiologically active materials having a small subcellular size such as yeast, bacteria, mold, enzymes or the like are suspended in an aqueous medium capable of gelation upon subsequent treatment of the suspending medium. Suitable suspending mediums include water soluble polymers. Representative suitable natural materials include kappa-carrageenan, iota-carrageenan, sodium alginate, furcellaran, zein, succinylated zein, succinylated cellulose, ethyl succinylated cellulose or the like. Representative suitable synthetic water soluble polymers include those formed from vinyl pyrolidone, 2-methyl-5-vinyl pyrridine-metnyl acrylate-methacrylic acid copolymer, vinyl alcohol, vinyl pyrridine, vinyl pyrridine-styrene copolymer or the like. The microbiologically active material is suspended in the suspending medium at a dilution which is selected using knowledge of the volume of the GMD to be produced and the density of size of cells or molecules in the first liquid medium.

The GMDs are formed so that there is a high probability that each GMD contains a desired number or less of microbiologically active material. This can be effected by regulating the dilution of the liquid composition to be processed to GMDs, a knowledge of the size of the microbiologically active material and the size of the GMDs to be produced. The regulation of these factors can be determined by conventional Poisson statistical analysis so that the number of GMDs containing more than the desired number of microbiologically active materials is more than two standard deviations from the mean.

Gel material and nutrients can be incorporated in the suspending medium, in which case very little dilution may be desired. Then, for example, when it is desired to have a high probability of zero or one microbiologically active material for GMDs, it is only necessary to dilute the sample by more than about a factor of about 1.1, usually up to about 10 or larger if desired if the unknown cell or enzyme concentration is believed to be large. For example, if the average volume ($V_{GMD}$) is about $10^{-7}$ ml, corresponding to a GMD with diameter about $5 \times 10^{-3}$ cm (50 $\mu$m), is spherical, dilution is generally not needed until the initial cell concentration reaches about $10^{+7}$ cells-ml$^{-1}$. For smaller spherical GMDs, for example, $10\mu$ diameter, dilution is not needed until the sample concentration reaches about $10^9$ cells-ml$^{-1}$. It is desirable, for example, to isolate zero or one microbiologically active cell per GMD in recombinant DNA research whereas it is desired to isolate a particularly active genetically altered bacteria such as *E. coli* capable of producing a desired molecule, e.g. interferon from a large population of such bacterium.

For purposes of sorting or isolating microbiologically active material, it is desirable to utilize dilutions such that the suspension can be subsequently formed into droplets each of which have a high probability of containing none of microbiologically active material or only a single cell or molecule of the microbiologically active material. By separating and localizing the biologically active material in this manner, it is possible to isolate materials of desired activity which activity is not diluted by the presence of other biologically active material not having the desired activity. For example, it may be desirable to isolate bacteria such as *E. coli*, altered by conventional recombinant DNA techniques, to produce a desired material such as a hormone, insulin, interferon, etc. In these techniques, DNA is altered on a batch basis and bacteria also is processed on a batch basis to effect implantation of a plasmid, said bacteria are then suspended in a liquid capable of forming a gel upon subsequent treatment and then converted into droplets such that there is a high probability that each droplet contains none or only one of such bacteria. The thus-produced liquid droplets are directed into a liquid medium capable of effecting gelation of the droplets. Alternatively, the initially liquid droplets are changed in temperature or contacted with suitable gel-inducing vapors before entering the second liquid medium. In addition, the gel droplets also can, but are not required to, contain a conventional bacterial growth supporting composition which permits the bacteria to replicate within the droplets. The suspension of such gel droplets then is treated in a conventional manner such as with a fluorescent dye, a fluorescent labeled antibody or fluorescent labeled antigen or the like in order to mark the gel droplets having the desired bacteria while preventing or greatly reducing the marking of the gel droplets not containing the desired bacteria.

This invention is useful for isolating a wide variety of materials having microbiological activity, interaction or suppression including parasites, virus, yeasts, cells, bacteria mold enzymes, interactions between variant cells, cell-virus interactions, hydrodomis or the like.

Representative bacteria which can be processed in accordance with this invention includes *E. coli, Bacillis subtilus,* Pseudomonas species, Clostridium, thermocellum, *Zymonanas mobilis, Methano bacterium sochngenii, Salmonella typhimurium, Serratia marcens, Clostridium botulinum, Bacillia sterothermophilis.* Any conventional tagging means can be utilized in order to identify the gel droplets containing the bacteria having the desired characteristics including radioactively labeled antibody, fluorescent antibody labeling, use of fluorescent dyes, viable stains, magnetic labeling or the like. These procedures are well known to be selective in labeling and/or staining products produced by bacteria. Similarly, the same techniques can be utilized for selectively identifying desired products of yeast, mold, parasites, etc.

In the case of molecular size biologically active molecules such as enzyme activity, or the accumulation or depletion of NADH or other fluorescent products or cofactors can be measured, the following procedure can be utilized in accordance with this invention. A sample containing unknown quantity of a particular enzyme is suspended, with modest dilution, in a first liquid medium which contains buffering compounds, substrates, cofactors and a gelling agent. When the approximate upper limit of the concentration of enzymes to be measured can be estimated, a GMD volume is selected so that there is a high probability the GMDs will contain either none or one enzyme molecule. When a linked enzyme assay is used, the appropriate additional enzymes, substrates and cofactors are also included. Similarly, if an assay is to be based on cell-cell interactions, one type of cell is also provided at relatively high concentrations. The resulting diluted sample is then passed through a vibrating orifice or nozzle or other means to cause formation of liquid droplets. As described previously, the liquid droplets are caused to enter the gel state by cooling, contacting with a suitable vapor or solid substrate or entering a second liquid medium. The resulting GMDs are coated with a thin layer impermeable or having controlled permeability to the substrates, products and/or cofactors of the enzyme catalyzed reaction, such as phosphatidyl ethanolamine or phosphatidyl choline or the like. For example, the permeability of the coating can be controlled to allow entry into the GMD of a reagent that effects marking, lysing or the like within the GMD and restricts outflow from the GMD of such marked product. The coated GMDs are maintained at a suitable temperature such that the enzyme reactions are carried out, not necessarily to completion, and fluorescent product is accumulated and retained in GMDs containing an enzyme molecule. Alternatively, a fluorescent substrate can be utilized, in which case the fluorescent substrate decreases or disappears in GMDs containing an enzyme molecule.

After the biologically active material within the gel micro-droplets has been treated in order to effect the desired change in the material, such as by incubation, mutation, staining with fluorescent stains, labeled with magnetically tagged or other immunological agents, the suspension of the gel micro-droplets then is processed in an apparatus having the capability of sensing a physical characteristic of individual gel micro-droplets to determine the presence or absence of a desired physical characteristic and thereafter isolating the gel micro-droplets having the desired physical characteristic. For example, the desired gel micro-droplets may be selectively stained with a fluorescent dye and can be passed one by one in a liquid stream by an optical analyzer capable of sensing the concentrated fluorescent dye on the gel micro-droplet. The analyzer controls means for isolating that portion of the liquid stream which satisfies the sensing criteria. For example, a portion of the liquid stream can be diverted into a secondary stream for subsequent recovery of the gel micro-droplets such as is disclosed by Kamentsky, U.S. Pat. No. 3,560,754. Alternatively, the mainstream can be converted into discrete droplets by being passed through a nozzle which is vibrated such as by a piezoelectric crystal by the means disclosed, for example, by Fylwyler, U.S. Pat. Nos. 3,710,933; 3,790,492 and 4,162,282. The drops containing the gel mciro-droplets having the desired characteristics then can be electrically charged selectively and then passed between a pair of deflecting plates in order to selectively divert the electrically charged droplets so that they can be recovered.

The process of this invention provides substantial advantages over the prior art processes in that microbiologically active material having a size much smaller than that of the normal cell, usually within the range of about 5 to 0.5 microns and even as small as molecular size materials, can be isolated to recover microbiologically active materials having a desired characteristic from a large population of such microbiologically active materials, the majority of which do not have the desired microbiological characteristic.

EXAMPLE I

Any of a variety of protocols for genetic manipulation is carried out on a large, for example about $10^9$ to about $10^{12}$ cells, population of bacteria such as $E.\ coli$ or the like, with the result that a small number, perhaps only one, or the cells of the post manipulation population have a new, desired feature such as the production of a specific biomolecule such as a specific protein or hormone or the like. Frequently, such biomolecules are not secreted, but are retained within the desired modified bacterium. Further, the desired modified bacterium typically obtains no selective growth characteristic which would allow use of conventional microbiological selection procedures. Instead, the desired modified bacterium must be sorted from the very large post manipulation population. An exemplary process for isolation begins by suspending the post manipulation population of $E.\ coli$ in a conventional medium such as YPD (containing yeast extract, potato starch and dextrose) but also 2% weight of sodium alginate, which suspension is in the pre-gel state. The suspension is then passed through a vibrating orifice nozzle such that the liquid stream breaks up into liquid droplets. Said liquid droplets are directed into a second liquid medium, typically stirred gently, 0.5% $CaCl_2$ at pH 7, where said liquid droplets rapidly exchange na ions for ca ions and enter the gel state. Gel formation typically occurs first at the outer surface of said liquid droplets, forming a temporary deformable skin, which deformable skin allows interfacial forces to direct the droplet into an approximately spherical or ellipsoid shape before the droplet is completely gelled. Within less than 1 to 15 minutes, depending on liquid droplet size and the KCl concentration, the transition into the gel state is complete. The GMDs are maintained in suspension by gentle stirring, and do not adhere to each other even after many hours. Additional nutrients such as glucose, ammonia, growth or medium such as YPD are supplied to the stirred medium such that the individual bacteria in each occupied GMD can grow and divide to form a microcolony. This incubation period is continued for several hours, typically about 5 to 10 hours, the exact hours depending on the volume of the GMDs which are used, until each initially occupied GMD is saturated or fully occupied. Any bacteria which are released into the liquid medium during said incubation are repelled from GMDs when the bacterial surface charge is the same sign as that of the outer surface of the GMDs and contamination and cross-contamination of GMDs is avoided. When the bacterial and GMD surface do not have the same surface charge, the GMDs are instead placed on the surface of a suitable filter such as a Nuclepore filter and gently washed, with flow through the filter such that any released bacteria are carried through the filter and do not contact other GMDs. In this case, it is often advantageous to select the original cell suspension concentration with respect to GMD volume such that there are many more unoccupied GMDs than GMDs occupied by one cell, which relationship greatly decreases the probability of occupied GMDs contacting each other on the surface of the filter. Following incubation either in suspension or retained on a filter surface, the GMDs contain a microcolony of $10^3$ to $10^5$ cells and are contacted typically for 1 second to 100 seconds, depending on GMD size with a chemical lysing agent such as Trition-X, sodium dodecyl sarcosinlate or sodium lauryl sarcosinlate. The brief exposure of GMDs to a chemical lysing agent results in lysing of cells mainly near the outer surface of the GMDs, with increasingly fewer lysed cells toward the center of the GMDs, and therefore increasing numbers of viable cells toward the center. The GMDs are now, or at the same time as the lysing agent, exposed to a fluorescent labelled antibody (FA); the antibody being preselected to be specific toward the desired protein or hormone. However, the exposure to the FA is usually different than to the lysing agent, said FA exposure usually being longer. A preferential staining of GMDs with released specific protein or hormone thereby occurs. The suspension of GMDs, now containing a few preferentially stained GMDs with viable cells near the center, is passed through a flow microfluorometer/cell sorter, such that the preferentially stained GMDs with viable cells near the center, is passed through a flow microflyorometer/cell sorter, such that the preferentially stained GMDs are isolated or sorted by the usual means now employed for isolating or sorting animal cells. Further incubation of the thus-isolated GMDs allows large and useful quantities of the rare, desirable modified $E.\ coli$ to be obtained and used.

I claim:

1. The process of selecting molecules or cells having a desired microbiological activity of a sample of a given material comprising the steps of:

(a) forming mutually independent samples of said material by
  (i) forming a dilute suspension of said material in a liquid diluent capable of forming a gel upon subsequent treatment, said dilute suspension having a dilution selected so that there is provided a high probability that each microsample produced from said suspension contains one or less microbiologically active molecule or cell;
  (ii) converting said suspension into gel droplets having a size between about 0.2 and 1000 microns,
  (iii) measuring a product of microbiological activity of each of said gel droplets independently of the other of said droplets and
(b) separating gel droplets displaying the desired microbiological activity.

2. The process of claim 1 wherein said droplets have a size between about 5 and 100 microns.

3. The process of claim 1 wherein said material is a bacterium.

4. The process of claim 3 wherein said bacterium is *E. coli*.

5. The process of claim 4 wherein said bacterium includes a genetically modified plasmid.

6. The process of claim 1 wherein said material is an enzyme.

7. The process of claim 1 wherein said material is a yeast.

8. The process of claim 1 wherein said material is a mold.

9. The process of claim 1 wherein said material comprises an animal cell.

10. The process of claim 1 wherein said material comprises a plant cell.

11. The process of any one of claims 1, 2, 3, 4, 6, 7, 8, 9, 10 or 5 wherein the microbiologically active material having the desired characteristic is selectively tagged with a marker composition capable of being sensed and sensing said marker composition of effect isolation of gel droplets containing the microbiologically active material having the desired characteristic.

12. The process of any one of claims 1, 2, 3, 4, 6, 7, 8, 9, 10 or 5 wherein the microbiologically active material having the desired characteristic produces a metabolite capable of being sensed and sensing said metabolite to effect isolation of gel micro-droplets containing the microbiologically active material having the desired characteristic.

13. The process of any one of claims 1, 2, 3, 4, 6, 7, 8, 9, 10 or 5 wherein the microbiologically active material having the desired characteristic coacts with a reagent within said mciro-droplet to product a reaction product capable of being sensed and sensing said reaction product to effect isolation of gel micro-droplets containing the microbiologically active material having the desired characteristic.

14. The process for selectively isolating gel micro-droplets containing a cell or molecule having microbiological activity having a desired microbiological characteristic from a large population of microbiologically active cells or molecules lacking said desired characteristic which comprises forming a dilute suspension of said population in a liquid diluent capable of forming a gel upon subsequent treatment, said dilution being selected so that there is provided a high probability that each sub-sample produced from said suspension contains one or less microbiologically active molecule or cell, converting said suspension into gel droplets having a size between about 0.2 microns and about 1000 microns sensing the gel droplets containing the microbiologically active material having the desired characteristic and selectively separating said gel droplets containing microbiologically active material having the desired characteristic from said population.

15. The process of claim 14 wherein said material is a bacterium.

16. The process of claim 15 wherein said bacterium is *E. coli*.

17. The process of claim 16 wherein said bacterium includes a genetically modified plasmid.

18. The process of claim 14 wherein said material is an enzyme.

19. The process of claim 14 wherein said material is a yeast.

20. The process of claim 14 wherein said material is a mold.

21. The process of claim 14 wherein the material comprises an animal cell.

22. The process of claim 14 wherein the material comprises a plant cell.

23. The process of any one of claims 14, 15, 16, 18, 19, 20, 21, 22 or 17 wherein the microbiologically active material having the desired characteristic is selectively tagged with a marker composition capable of being sensed and sensing said marker composition to effect isolation of gel droplets containing the microbiologically active material having the desired characteristic.

24. The process of any one of claims 14, 15, 16, 18, 19, 20, 21, 22 or 17 wherein the microbiologically active material having the desired characteristic produces a metabolite capable of being sensed and sensing said metabolite to effect isolation of gel micro-droplets containing the microbiologically active material having the desired characteristic.

25. The process of any one of claims 14, 15, 16, 18, 19, 20, 21, 22 or 17 wherein the microbiologically active material having the desired characteristic coacts with a reagent within said mciro-droplet to produce a reaction product capable of being sensed and sensing said reaction product to effect isolation of gel micro-droplets containing the microbiologically active material having the desired characteristic.

* * * * *